US010932942B2

United States Patent
Zani et al.

(10) Patent No.: US 10,932,942 B2
(45) Date of Patent: Mar. 2, 2021

(54) DRAINAGE BAG SYSTEMS INCLUDING AT LEAST ONE INDICATOR ELEMENT AND METHODS OF USING THE SAME

(71) Applicant: C.R. BARD, INC., Murray Hill, NJ (US)

(72) Inventors: Paul Anthony Zani, Franklin, TN (US); John Christian Gohde, Decatur, GA (US); Allan Jon Cetrone, Woodbury, CT (US); Uriyah Duchun Robinson, Atlanta, GA (US)

(73) Assignee: C.R. BARD, INC., Murray Hill, NJ (US)

( * ) Notice: Subject to any disclaimer, the term of this patent is extended or adjusted under 35 U.S.C. 154(b) by 418 days.

(21) Appl. No.: 15/324,114

(22) PCT Filed: Jan. 29, 2016

(86) PCT No.: PCT/US2016/015795
§ 371 (c)(1),
(2) Date: Jan. 5, 2017

(87) PCT Pub. No.: WO2016/126555
PCT Pub. Date: Aug. 11, 2016

(65) Prior Publication Data
US 2017/0202698 A1    Jul. 20, 2017

Related U.S. Application Data

(60) Provisional application No. 62/111,088, filed on Feb. 2, 2015, provisional application No. 62/249,752, filed on Nov. 2, 2015.

(51) Int. Cl.
*A61F 5/44*       (2006.01)
*A61F 5/451*      (2006.01)
(Continued)

(52) U.S. Cl.
CPC .............. *A61F 5/4404* (2013.01); *A61F 5/44* (2013.01); *A61F 5/451* (2013.01); *B65D 33/004* (2013.01); *A61B 50/33* (2016.02); *B08B 1/006* (2013.01)

(58) Field of Classification Search
CPC .......... A61F 5/4404; A61F 5/44; A61F 5/451; A61B 50/33; B08B 1/006; B65D 33/004
(Continued)

(56) References Cited

U.S. PATENT DOCUMENTS 3,329,261 A    7/1967  Serany et al.
5,286,262 A *  2/1994  Herweck ............. A61M 1/0013
                                                         604/317
(Continued)

FOREIGN PATENT DOCUMENTS

JP    H08131470 A    5/1996
JP    2000507872 A   6/2000
(Continued)

OTHER PUBLICATIONS

Alaska DHHS ("Indwelling (Foley) Catheter Care." Alaska Department of Health and Social Services, Mar. 31, 2014, dhss.alaska.gov/daph/Docurnents/policies/N-13%20Indwelling%20(Foley)%20catheter%20care.pdf.) (Year: 2014).*
(Continued)

*Primary Examiner* — Andrew J Mensh
(74) *Attorney, Agent, or Firm* — Dorsey & Whitney LLP

(57) ABSTRACT

Embodiments disclosed herein relate to drainage bag systems (e.g., catheterization and urine drainage bag systems) including at least one indicator element that may indicate that one or more patient care protocols were performed. For example, the drainage bag system includes a drainage bag including at least one indicator element (e.g., calendar, checklist, combinations thereof, etc.) configured to provide
(Continued)

information indicating that the one or more patient care protocols were performed, such as verifying compliance with the one or more patient care protocols.

22 Claims, 9 Drawing Sheets

(51) Int. Cl.
  *B65D 33/00* (2006.01)
  *A61B 50/33* (2016.01)
  *B08B 1/00* (2006.01)
(58) Field of Classification Search
  USPC .......................................................... 604/318
  See application file for complete search history.

(56) References Cited

U.S. PATENT DOCUMENTS

| | | | |
|---|---|---|---|
| 6,579,271 | B1 | 6/2003 | Aruffo et al. |
| 6,640,976 | B1* | 11/2003 | Franks-Farah ......... A61B 50/31 |
| | | | 206/232 |
| 6,740,068 | B1* | 5/2004 | Aruffo .................... A61F 17/00 |
| | | | 206/570 |
| 8,678,190 | B2* | 3/2014 | Tomes ................... A61M 25/00 |
| | | | 206/571 |
| 2001/0044427 | A1 | 11/2001 | Mazel et al. |
| 2004/0056478 | A1 | 3/2004 | Bruce |
| 2006/0219595 | A1 | 10/2006 | Peters |
| 2008/0102238 | A1* | 5/2008 | Swords ................. G09F 3/0292 |
| | | | 428/40.1 |
| 2008/0249482 | A1 | 10/2008 | Erez |
| 2009/0089099 | A1 | 4/2009 | Kranz et al. |
| 2009/0118330 | A1 | 5/2009 | Abramo et al. |
| 2009/0128330 | A1* | 5/2009 | Monroe ................ A61M 5/002 |
| | | | 340/568.1 |
| 2010/0274205 | A1 | 10/2010 | Morelli et al. |
| 2011/0232234 | A1* | 9/2011 | Lockwood ............ A61M 25/00 |
| | | | 53/443 |
| 2011/0290262 | A1 | 12/2011 | Tomes et al. |
| 2011/0297147 | A1* | 12/2011 | Lick ..................... G09B 19/003 |
| | | | 128/202.16 |
| 2012/0184944 | A1 | 7/2012 | Tomes et al. |
| 2014/0336598 | A1 | 11/2014 | Christensen |

FOREIGN PATENT DOCUMENTS

| | | |
|---|---|---|
| JP | 2004314621 A | 11/2004 |
| JP | 3139221 B2 | 1/2008 |
| JP | 2009509703 A | 3/2009 |
| JP | 2012254306 A | 12/2012 |
| JP | 2013176512 A | 9/2013 |
| JP | 2015501192 A | 1/2015 |
| WO | 02053209 A1 | 7/2002 |
| WO | 2016126555 A1 | 8/2016 |

OTHER PUBLICATIONS

Advisory Action for U.S. Appl. No. 15/479,833 dated Oct. 4, 2018.
Final Office Action for U.S. Appl. No. 15/479,833 dated Jul. 26, 2018.
Advisory Action for U.S. Appl. No. 15/479,833 dated Mar. 29, 2018.
International Search Report and Written Opinion from International Application No. PCT/US2016/015795 dated May 13, 2016.
Non-Final Office Action for U.S. Appl. No. 15/479,833 dated Jul. 26, 2017.
Restriction Requirement for U.S. Appl. No. 15/479,833 dated Jun. 14, 2017.
U.S. Appl. No. 15/324,114, filed Jan. 5, 2017.
Gould, et al., "Guideline for Prevention of Catheter Associated Urinary Tract Infections 2009," HICPAC, Center of Disease Control ("CDC"), 2009, pp. 1-67, http://www.cdc.gov /hicpac/pdf/cauti/cautiguideline2009final.pdf.
U.S. Appl. No. 62/111,088, filed Feb. 2, 2015.
U.S. Appl. No. 62/249,752, filed Nov. 2, 2015.
Notice of Allowance for U.S. Appl. No. 15/479,833 dated Nov. 18, 2020.

* cited by examiner

DRAINAGE BAG SYSTEMS INCLUDING AT LEAST ONE INDICATOR ELEMENT AND METHODS OF USING THE SAME

CROSS-REFERENCE TO RELATED APPLICATION

This application claims priority to U.S. Provisional Application No. 62/111,088 filed on 2 Feb. 2015 and U.S. Provisional Application No. 62/249,752 filed on 2 Nov. 2015, the disclosure of each of the foregoing applications is incorporated herein, in its entirety, by this reference.

BACKGROUND

Generally, urinary catheterization involves insertion of a urinary catheter (e.g., a tube) through a patient's urethra into a bladder. The urinary catheter (e.g., a Foley urinary catheter) allows the patient's urine to drain from the bladder through a drainage tube into a drainage bag.

In some instances, a care provider may have protocols related to patient care during and/or after the patient's catheterization. However, such patient care protocols may be inconsistently performed and/or performed inaccurately. Improving compliance with such patient care protocols may improve patient care and/or reduce complications related to the patient's catheterization (e.g., catheter-associated urinary tract infection).

Accordingly, manufacturers and users of catheterization systems and methods continue to seek improvements thereto.

SUMMARY

Embodiments disclosed herein relate to drainage bag systems (e.g., catheterization and urine drainage bag systems) including at least one indicator element that may indicate that one or more patient care protocols were performed. For example, the drainage bag system includes a drainage bag including at least one indicator element (e.g., calendar, checklist, combinations thereof, etc.) configured to provide information indicating that the one or more patient care protocols were performed, such as verifying compliance with the one or more patient care protocols.

In an embodiment, a drainage bag system is disclosed. The drainage bag system includes a drainage bag. The drainage bag includes an inlet configured to receive a fluid from a patient. The drainage bag also includes one or more panels defining an interior space configured to hold the fluid therein. The drainage bag system further includes at least one indicator element. The at least one indicator element includes one or more indicator sites thereon. Each of the one or more indicator sites includes at least one of a blank or unfilled location.

In an embodiment, a method of using a drainage bag is disclosed. The method includes providing a drainage bag system to be operably connected to a patient. The drainage bag system includes the drainage bag defining an interior space configured to contain fluid. The drainage bag system also includes at least one indicator element including one or more indicator sites thereon. Each of the one or more indicator sites includes at least one of a blank or unfilled location. The method further includes performing one or more patient care protocols on the patient that is related to using the drainage bag with the patient. The method additionally includes marking the one or more indicator sites to show that the one or more patient care protocols were performed.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, the like elements have been designated by like reference numbers throughout the various accompanying figures. Understanding that these drawings depict only typical embodiments of the present disclosure and are not therefore to be considered to be limiting of its scope, the embodiments of the present disclosure will be described and explained with additional specificity and detail through the use of the accompanying drawings in which.

DETAILED DESCRIPTION

Figure 1A:
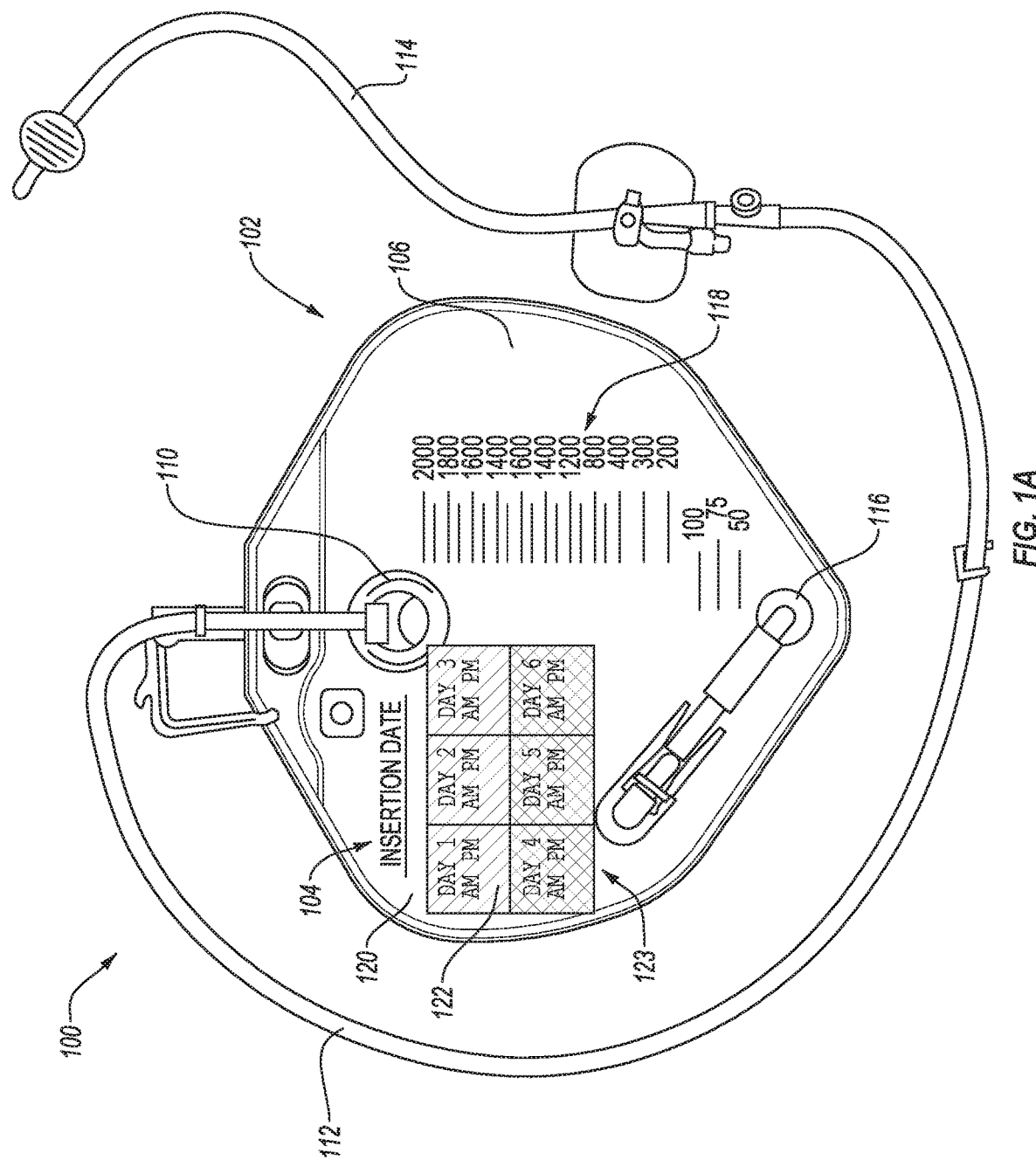
FIG. 1A is a top plan view of a drainage bag system that includes a drainage bag having at least one indicator element in an inactive state, according to an embodiment.

Embodiments disclosed herein relate to drainage bag systems (e.g., catheterization and urine drainage bag systems) including at least one indicator element that may indicate that one or more patient care protocols were performed. For example, the drainage bag system includes a drainage bag including at least one indicator element (e.g., calendar, checklist, combinations thereof, etc.) configured to provide information indicating that the one or more patient care protocols were performed, such as verifying compliance with the one or more patient care protocols.

The indicator element of the drainage bag may be in a first or an inactive state (e.g., during initial deployment of the drainage bag). The indicator element may be reconfigured into a second or active state, to provide information related to the patient's care, status of the urine drainage bag, etc. For example, in the active state, the indicator element may provide or display information related to one or more patient care protocols. Such information may include one or more of a date of deployment of the drainage bag, a date of insertion of a catheter operably connected to the drainage bag, date(s) and/or performance of the one or more patient care protocols, etc., which may be required and/or recommended by the one or more patient care protocols.

The indicator element of the drainage bag may be reconfigured from the inactive state to the active state in a manner that facilitates authentication of the accuracy of the information related to patient care protocols provided or displayed by the at least one indicator element and/or prevents tampering therewith (e.g., compliance indicator elements). In an embodiment, the indicator element may be reconfigured from the inactive state into the active state using a specific and/or unique token. For example, the token may become available to the user (e.g., a medical practitioner) after starting or completing a predetermined task or sequence of tasks.

The one or more patient care protocols may vary depending on the application of drainage bag system (e.g., collect urine, blood, stool, etc.) and the specific needs of the patient. In an embodiment, the drainage bag may include a urine drainage bag. In such an embodiment, at least some of the patient care protocols may be configured to comply with the Center of Disease Control's ("CDC") "Guideline for Prevention of Catheter Associated Urinary Tract Infections" released in 2009 and available at http://www.cdc.gov/hicpac/pdf/CAUTI/CAUTIguideline2009final.pdf, the disclosure of which is incorporated herein, in its entirety, by this reference. For example, the one or more patient care protocols verified by the at least one indicator element of the urine drainage bag may include one or more of the following: periodic cleaning of the perineal region of the patient, periodic cleaning of the periurethral region of the patient, periodic cleaning of a portion of the drainage bag system (e.g., about every 12 hours), routine removal of urine from the drainage bag, inspections of the drainage bag system to check for leaks, kinks, etc., proper hand hygiene when manipulating the drainage bag system, or proper aseptic techniques performed while inserting the urinary catheter.

The drainage bag systems disclosed herein are described as being urinary drainage bag systems. However, the drainage bag systems disclosed herein may be used in any drainage bag system that collects fluid from a patient. For example, any of the drainage bag systems disclosed herein may be used in a blood drainage system, a pleural drainage system, a peritoneal drainage system, a bowel drainage system (e.g., a stool collection bag), or another suitable drainage system.

FIG. 1A is a top plan view of a drainage bag system 100 that includes a drainage bag 102 having at least one indicator element 104 in an inactive state, according to an embodiment. The drainage bag 102 includes a front panel 106 and a back panel bonded together to form a fluid tight container. However, in other embodiments, the drainage bag 102 may include and/or may be formed by three or more panels, or a single body. The one or more panels may define an interior space configured to hold a fluid (e.g., urine) therein. In an embodiment, a privacy barrier (not shown) may be provided that is integrally formed with the drainage bag 102, attached to the drainage bag 102, or separate from the drainage bag 102, which is at least substantially opaque and configured to cover at least a portion of the drainage bag 102 (e.g., obscure the at least a portion of an interior space of the drainage bag 102 from view such as obscuring and/or concealing urine in the drainage bag 102). Moreover, it should be appreciated that the one or more panels of the drainage bag 102 may include flexible, rigid, resilient, or any suitable material or combinations of materials. In any event, the panels of the drainage bag 102 may be connected and/or bonded together in a manner that forms or defines the interior space of the drainage bag 102, which may contain fluid therein.

Generally, the drainage bag 102 may have any suitable geometry. In the illustrated embodiment, the drainage bag 102 has a generally tear-shaped geometry. However, the drainage bag 102 may have a generally circular geometry, a generally rectangular geometry, etc.

The drainage bag 102 may also include an inlet 110, which may be configured to accept a fluid flow from the patient (e.g., urine) into the drainage bag 102. For example, the inlet 110 may receive or connect to a drainage tube 112 that may be in fluid communication with a catheter 114 that, for example, may be positioned in a patient's bladder. In the illustrated embodiment, the catheter 114 may include a Foley urinary catheter, such that urine may flow into the drainage bag 102 from the catheter 114 and through the drainage tube 112.

In an embodiment, the drainage bag 102 may include an outlet 116 (e.g., at or near a bottom of the drainage bag 102). For example, the outlet 116 may be configured to allow a fluid collected in the drainage bag 102 to flow or drain from the drainage bag 102 (e.g., for collecting or extracting the fluid from the drainage bag 102). For example, the outlet 116 may include the Safety-Flow™ outlet device or another similar outlet device.

The front panel 106 of the drainage bag 102 may further include one or more graduated markings 118 that may indicate an amount of a fluid collected in the drainage bag 102. For example, the graduated markings 118 may facilitate determining the amount of fluid discharged by the patient in a time span (e.g., predetermined time span). In some embodiments, the graduated marking 118 may facilitate determining or approximating a time and/or date for draining, removing, and/or changing out the drainage bag 102.

The indicator element 104 may be configured to show completion of a task (e.g., a patient care protocol) related to the drainage bag system 100. For example, the indicator element 104 may be marked by a user to show that a task has been performed. In an embodiment, the indicator element 104 may be a compliance indicator element configured to ensure compliance with one or more patient care protocols. For example, the indicator element 104 may include a type identifier 120 that provides general information to the user. The indicator element 104 may also include one or more indicator sites 122 that are marked by a user. For example, the indicator sites 122 may be configured to verify compliance with the one or more patient care protocols (e.g., compliance indicator sites).

The type identifier 120 may provide information related to the drainage bag 102 and/or patient care. For example, the type identifier 120 may include information related to the patient (e.g., the patient's name, the procedure performed on the patient, etc.), information related to the caregiver (e.g., the responsible physician's name, the responsible nurse's name, etc.), the catheter 114 insertion date, etc. The type identifier 120 may also identify what patient care protocols are being indicated as having been performed and/or verified by the indicator sites 122. The type identifier 120 is not configured to verify performance of the one or more patient care protocols.

In an embodiment, the type identifier 120 may be configured to be marked by a user. For example, the type identifier 120 may include a surface that is configured to be marked using writing utensils, receive a token (e.g., sticker, stamp, etc.), or other suitable forms of input. Marking the type identifier 120 may enable the indicator element 104 to display information that may be unique to each individual drainage bag 102. In some embodiments, at least a portion of the type identifier 120 may be preprinted. The preprinted portions may include information related to the patient care protocols tracked by the indicator sites 122 and/or facilitate marking the type identifier 120. For example, the preprinted portions of the type identifier 120 may include the phrase "Insertion Date:", "Patient Name:", "Physician;" similar phrases, or combinations thereof. Adjacent to the preprinted portions, the type identifier 120 may include a surface configured to receive input from the user.

In an embodiment, the type identifier 120 may include labeling (not shown) that facilitates performance and standardization of the one or more patient care protocols verified by the compliance indicator sites. The labeling may include step-by-step instructions and/or pictographs detailing how to perform the one or more patient care protocols verified by the compliance indicator sites. The labeling may conform to patient care protocols promulgated by the CDC, individual hospitals, or other healthcare organizations. Having the instructions included in the type identifier 120 may help standardize the one or more patient care protocols, prevent a user (e.g., a physician, nurse, certified nurse's assistant, etc.) from incorrectly performing the one or more patient care protocols, refresh the user's memory on how to correctly perform the one or more patient care protocols, etc. As such, the labeling may further verify compliance with the one or more patient care protocols.

The indicator sites 122 may be configured to be marked by a user to indicate that a task related to the drainage bag system 100 has be performed. For example, the indicator sites 122 may be compliance indicator sites configured to verify compliance with one or more patient care protocols. Each of the indicator sites 122 may include a blank or unfilled location that corresponds to one or more patient care protocols that may be performed. The blank or unfilled locations may be configured to be marked by a user, for example, when one or more patient care protocols are performed. For example, the blank or unfilled locations may be marked just before, during, or after the one or more patient care protocols are performed. As such, the indicator sites 122 may be configured to be marked using a writing utensil, at least one token, or another suitable form of input. As such, marking the indicator sites 122 may indicate and verify compliance with a patient care protocol (e.g., compliance indicator sites).

In some embodiments, the indicator sites 122 may include one or more markings thereon (e.g., preprinted thereon) configured to facilitate marking by the user. For example, the indicator sites 122 may include a box defining at least one indicator site 122, an underlined portion indicating where to mark, one or more phrases (e.g., "_____/_____/20_____" indicating a date to be marked), etc.

In the illustrated embodiment, the indicator sites 122 at least partially form a calendar 123 (e.g., an indicator displaying one or more dates). In an embodiment, the calendar 123 may be configured to verify compliance with one or more patient care protocols. For example, each of the of the indicator sites 122 may be compliance indicator sites that may correspond to a date (e.g., calendar date), day (e.g., number of days after an event), and/or time that the one or more patient care protocols are to be performed and/or verify when the one or more patient care protocols are performed. In the illustrated embodiment, the calendar 123 has less than 31 indicator sites 122 (e.g., less than 30 indicator sites 122). However, in other embodiments, the calendar 123 may include at least 30 indicator sites 122 (e.g., 31 indicator sites 122) to correspond to each day of a given month of a year. The indicator sites 122 may at least partially form the calendar 123 if the one or more patient care protocols are to be performed at certain time intervals, on certain dates and/or times; or it is desirable to track the performance of the one or more patient care protocols over a period of time. Such patient care protocols may include, for example, washing the perineal and/or periurethral region of the patient if the drainage bag 102 is used with the urinary catheter 114, periodic inspections of the drainage bag system 400 by the user, etc.

In an embodiment, at least some of the dates provided on the calendar 123 may exhibit different colors. For example, the calendar 123 may include a first time period (e.g., including one or more days) that exhibits a first color and a second time period that exhibits a second color. In an embodiment, the different colors may be used to indicate when the catheter 114 (e.g., the catheter 114 that operably connected to the drainage bag 102) should be removed from the patient. For example, the first time period of the calendar 123 may represent the CDC's recommend time period that the catheter 114 is inserted into the patient (e.g., about one to three days). The calendar 123 may also include a second time period immediately after the first time period that exhibits a different color than the first time period. As such, the second time period may indicate that the CDC recommends removing the catheter 114 from the patient. Additionally, the calendar 123 may include one or more additional time periods immediately after the second time period that exhibit a color that is different than the first time period and the second time period. In other embodiments, the one or more colors may indicate time periods within which one or more specific patient care protocols may be performed, when the one or more patient care protocols change, etc.

In an embodiment, the indicator element 104 may initially be in an inactive state (FIG. 1A). The indicator element 104 is considered to be in an inactive state when the type identifier 120 and/or each indicator site 122 include a blank or unfilled location. For example, the type identifier 120 that is in an inactive state does not provide any information and instead merely provides a location to receive input. Similarly, the indicator sites 122 that are in an inactive state merely provide locations that are configured to be marked by the user and/or indicate that no patient care protocols have been performed.

Figure 1B:
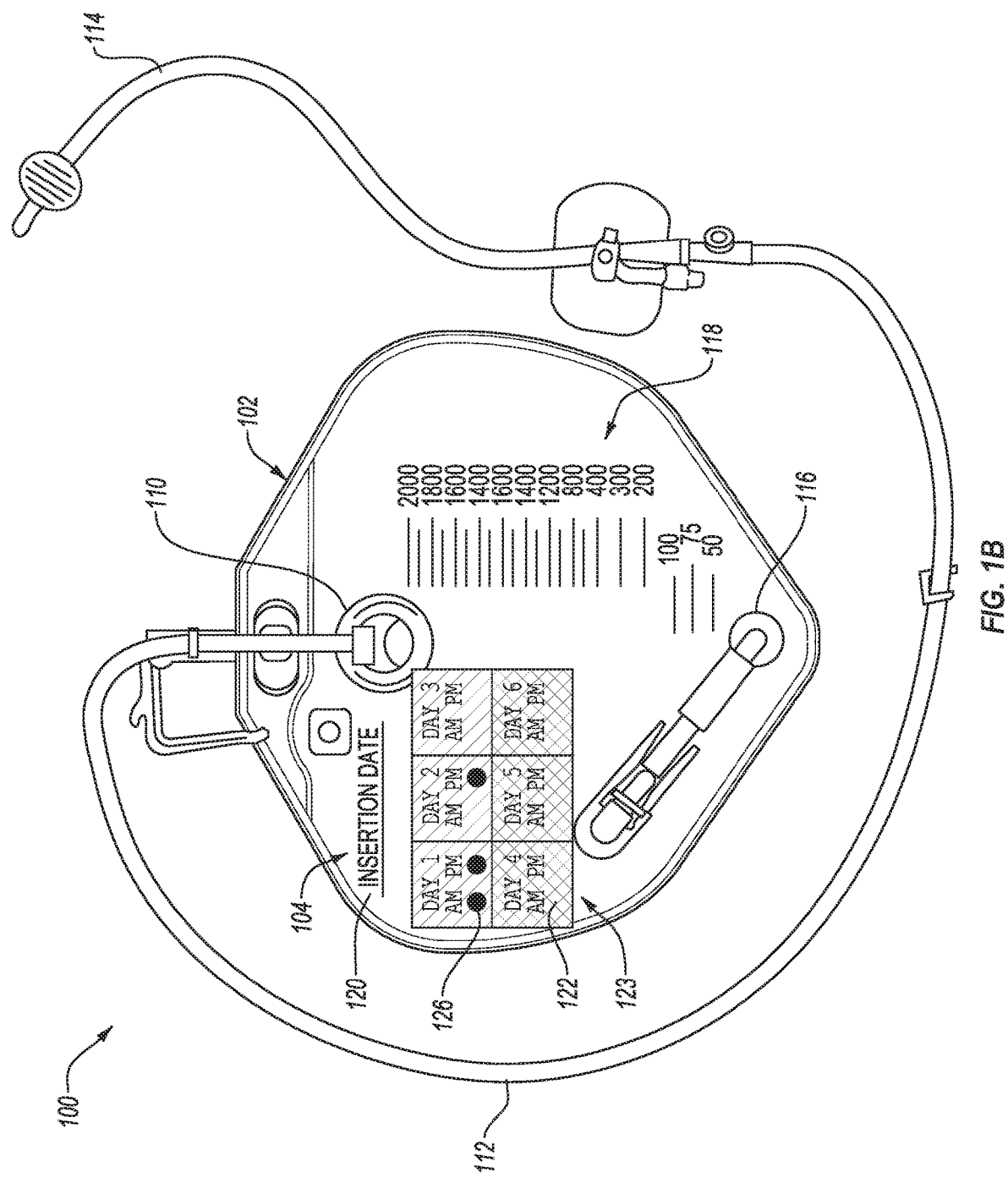
FIG. 1B is a top plan view of the drainage bag system shown in FIG. 1A having an indicator element in an active state, according to an embodiment.

However, the indicator elements 104 may be reconfigured from an inactive state to an active state when the type identifier 120 and/or at least one of the indicator sites 122 are marked by the user. FIG. 1B is a top plan view of the drainage bag system 100 shown in FIG. 1A having the indicator element 104 in an active state, according to an embodiment. As such, when the indicator element 104 is in an active state, the type identifier 120 may provide general information about the drainage bag 102 and/or patient care while the indicator sites 122 may indicate that a task related to the drainage bag system 100 has been performed (e.g., verify compliance with one or more patient care protocols and/or that one or more patient care protocols have been performed). For example, in the illustrated embodiment, the indicator sites 122 includes compliance indicator sites in an active state that show that patient care protocols have been performed at least three times over a two day period. However, the illustrated indicator sites 122 include compliance indicator sites that also show that at least one patient care protocol may not have been performed. In some embodiments, the type identifier 120 may initially be in an active state. For example, all the information provided by the type identifier 120 may be preprinted on the indicator element 104.

The indicator sites 122 may be configured to be marked by the user using different mechanisms. In an embodiment, the indicator sites 122 may include or provide one or more locations (e.g., surfaces) that may be marked using at least one writing utensil (e.g., marker, etc.). For example, the indicator sites 122 may include paper or another surface that may be marked mark by the writing utensil. The indicator sites 122 may be configured to be marked in a specific manner, such as with a date or a symbol identifying the user (e.g., signature, initials, etc.). In some embodiments, the indicator sites 122 may be include material that may only be marked using a specific writing utensil. For example, the indicator sites 122 may include one or more dark or black locations, which may accept markings from a light-colored writing utensil.

Figure 1C:
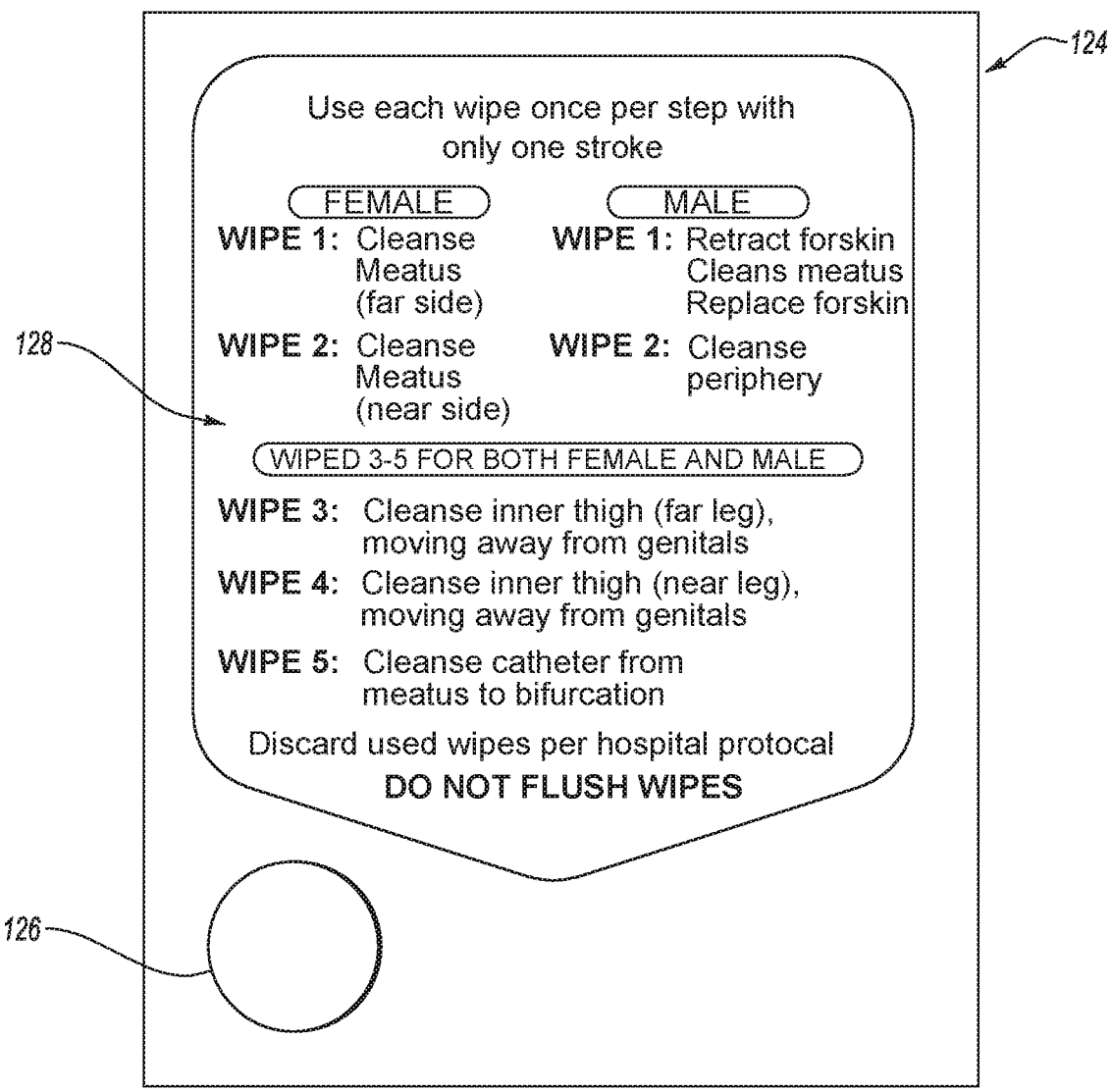
FIG. 1C is a top plan view of a package that may form a portion of the drainage bag system shown in FIG. 1A, according to an embodiment.

Alternatively or additionally, the indicator sites 122 may be configured to be marked using at least one token 126 (see FIGS. 1B and 1C). The token 126 may be any suitable identifying marking that may be placed, attached, stamped, or otherwise imposed on the indicator sites 122. For example, the token 126 may be a sticker, a stamp, paper, etc. that includes an adhesive thereon that adheres to the drainage bag 102. In some embodiments, the token 126 may be a specific token. For example, the token 126 may exhibit a specific size, shape, color, or combinations thereof; and/or may have a specific symbol printed thereon (e.g., a user's name). In some embodiments, the token 126 may only be accessed at certain times, thereby reducing or eliminating incorrect or backdated markings on the indicator element 104.

The indicator element 104 may be positioned on the drainage bag 102. For example, the drainage bag 102 may have a geometry that includes or provides a suitable location for the indicator element 104. For example, the indicator element 104 may be placed in a location that may not be covered or obscured by the inlet 110, the outlet 116, the drainage tube 112, or any other device of the drainage bag system 100. Additionally or alternatively, the indicator element 104 may be spaced or distanced from the graduated markings 118.

In any event, the indicator element 104 may be located on any panel or portion of the drainage bag 102. For example, the indicator element 104 may be attached to the front panel 106, the back panel, or the privacy barrier. Moreover, it should be appreciated that references to the front panel 106 and back panel of the drainage bag 102 are made for ease of description, and either panel of the drainage bag 102 may be considered as the front or back panel thereof. In the illustrated embodiment, the indicator element 104 may be located on the front panel 106 of the drainage bag 102. For example, the indicator element 104 may provide information to the user if the front panel 106 of the drainage bag 102 is generally facing the user. In alternative or additional embodiments, the drainage bag 102 may include multiple indicator elements (e.g., the indicator element 104 may be provided or included on the front panel 106 and another indicator element may be included on the back panel of the drainage bag 102), which may increase the likelihood that at least one of the indicator elements will generally face the user under some use conditions.

The indicator element 104 and/or portions thereof may have any number suitable sizes or dimensions, which may vary from one embodiment to the next. In some embodiments, the indicator element 104 may have relatively large dimensions, which may improve visibility thereof from a distance. In other embodiments, one or more portions of the indicator element 104 may have relatively small dimensions, which may facilitate display of additional information (as compared with the larger indicator element or corresponding portions thereof). In an embodiment, the indicator element 104 may be configured to provide or display (e.g., to a user, such as a health care provider) information related to one or more patient care protocols.

In an embodiment, one or more portions or elements of the indicator element 104 may be preprinted on, attached to, or secured to the drainage bag 102. For example, at least a portion of the type identifier 120 and/or the indicator sites 122 may be printed on the front panel 106, the back panel, and/or the privacy barrier of the drainage bag 102. In other embodiments, at least a portion of the indicator element 104 (e.g., at least one of the type identifier 120 and/or indicator sites 122) may be printed on a device (e.g., paper, sticker, stamp, etc.) that is attached to the front panel 106, the back panel, or the privacy barrier of the drainage bag 102. The device that includes at least a portion of the indicator element 104 may be provided from, for example, a package 124 (FIG. 1C). For example, the drainage bag system 100 may not initially include the indicator element 104 and the indicator element 104 is added to the drainage bag system 100 after the drainage bag system 100 is provided (e.g., after opening a kit, after insertion of the catheter 114, etc.)

In some embodiments, the drainage bag system 100 may include one or more patient care protocol packages 124 ("packages"). FIG. 1C is a top plan view of a package 124 that may form a portion of the drainage bag system 100, according to an embodiment. The package 124 may include any device (e.g., token 126) that is configured to perform, verify, and/or assist at least one of the one or more patient care protocols or the device may be omitted. In an embodiment, the package 124 may be configured to perform and/or assist at least one of the one or more patient care protocols that are verified by the indicator sites 122 (e.g., compliance indicator sites). For example, in the illustrated embodiment, the package 124 is a wipe container. The wipes present in the package 124 may be used to wash one or more regions of the patient and/or one or more portions of the drainage bag system 100 according to one or more patient care protocols. The package 124 may include other devices, such as syringes used to remove fluid from the drainage bag 102, a container including gloves therein, or combinations thereof.

In some embodiments, the package 124 may include at least one token 126 associated (e.g., attached to, positioned within, incorporated into, etc.) therewith. For example, the at least one token 126 may be positioned on a surface of the package 124. The token 126 is configured to be removed from the package 124 and attached to the indicator sites 122. Positioning the token 126 on the package 124 permits the user to only have access to the token 126 just before, during, and for a short period of time after one or more patient care protocols are performed. Restricting the time period during which the user has access to and can mark the indicator sites 122 with the token 126 may further verify compliance with the one or more patient care protocols (e.g., compliance indicator sites). In particular, restricting when a user has access to the token 126 reduces or eliminates incorrect or backdated markings of the compliance indicator sites.

In an embodiment, the token 126 may be positioned on the surface of the package 124 such that the token 126 acts as a tamper proof seal. For example, the token 126 may straddle and/or cover a portion of an exterior surface of the package 124 that is configured to grant access to an interior region of the package 124 or be otherwise used. As such, an at least partially torn token 126 or a missing token 126 may indicate that the package 124 may have been tampered with.

In some embodiments, the indicator sites 122 may be configured to receive the token 126 from the package 124. For example, the indicator sites 122 may exhibit a size and/or shape that correspond to the size and/or shape of the token 126 on the package 124.

In an embodiment, the token 126 may be positioned within the package 124. As such, the token 126 positioned within the package 124 may only be accessed after the package 124 is opened. For example, the token 126 may be positioned under the wipes that are within the package 124 such that the token 126 may only be accessed after the wipes are removed from the package 124. The token 126 positioned within the package 124 may be used in conjunction with the token 126 positioned on the surface of the package 124. In other embodiments, at least one of the token 126 positioned within the package 124 or the token 126 positioned on the surface of the package 124 may be omitted.

In an embodiment, the package 124 may include labeling 128 that facilitates performance and standardization of the one or more patient care protocols. In some embodiments, the labeling 128 may facilitate correct usage of the package 124 and correct performance of the one or more patient care protocols that use the package 124. For example, the labeling 128 may include step-by-step instructions and/or pictographs detailing how to perform the one or more patient care protocols that utilize the package and/or how to correctly use the package 124. The labeling 128 may conform to patient care protocols promulgated by the CDC, individual hospitals, other healthcare organizations, or combinations thereof. Having the labeling 128 included on the package 124 (e.g., preprinted on the package 124) may help standardize the one or more patient care protocols that utilize the package 124, standardize the operation of the package 124, prevent a user from incorrectly performing the one or more patient care protocols and/or incorrectly using the package 124, refresh the user's memory on how to correctly use the package 124, etc. As such, the instructions may further verify compliance with the one or more patient care protocols.

In an embodiment, the package 124 may further include the indicator element 104 therein or thereon. For example, the indicator element 104 may include a sticker, a piece of paper, a postcard-like device, etc. that is attached to and/or positioned within the package 124. The indicator element 104 may then be removed from the package 124 and attached to the drainage bag system 100, such as attached to the drainage bag 102. For example, the indicator element 104 may be attached to the front panel 106, the back panel, the privacy barrier, or otherwise associated with the drainage bag 102 (FIGS. 4A-4D). In an embodiment, the indicator element 104 may be attached to the drainage bag system 100 using an adhesive, a string, an elastic band, a clamp, or another attachment method.

FIGS. 1A-1C also illustrate a method of using the drainage bag system 100, according to an embodiment. Referring to FIG. 1A, the drainage bag system 100 may be provided, which may be configured to be used as a urinary drainage bag system including the catheter 114. In such an embodiment, the indicator element 104 may be configured to indicate completion of a task related to the drainage bag system 100 (e.g., verify performance and/or compliance with one or more patient care protocols related to pre-insertion of the catheter 114 and/or post-insertion of the catheter 114). For example, the indicator element 104 may include compliance indicator elements configured to verify compliance with the post-insertion patient care protocol of washing portions of the periurethral and perineal regions of the patient, and/or washing portions of the drainage bag system 100, in particular, portions of the drainage bag system 100 positioned proximate the periurethral and perineal regions of the patient ("post-insertion patient care protocol"). In some embodiments, the post-insertion patient care protocol may be required to be performed about every 12 hours. As such, the indicator element 104 may include the calendar 123 where each date on the calendar 123 includes two indicator sites 122 that correspond to one of the 12 hour periods. Initially, the indicator element 104 may be provided in an inactive state.

Referring to FIG. 1C, in the illustrated embodiment, the package 124 may be used to facilitate performance of a patient care protocol related to the drainage bag system 100. In an embodiment, the package 124 may also be configured to verify compliance with a patient care protocol (e.g., the post-insertion patient care protocol). For example, the package 124 may include a container that includes wipes therein. In some embodiments, the post-insertion patient care protocol may require that five different portions of the patient's periurethral region, the patient's perineal region, and the drainage bag system 100 be washed using, for example, non-antiseptic wipes. As such, the package 124 may include at least five different wipes therein, each wipe corresponding to a different portion of the patient's periurethral region, the patient's perineal region, and the drainage bag system 100. An example of wipes that may be included in the package 124 include Provon® products available from GOJO.com.

The package 124 may include labeling 128 thereon that facilitates performance and standardization of the post-insertion patient care protocol. For example, the illustrated labeling 128 may state that the first and second wipes present in the package 124 may be used to clean the genitalia of the male (e.g., wipe the foreskin and the meatus, foreskin, the periphery thereabout) and/or female (wipe the meatus). The labeling 128 may also state that the third and fourth wipe present in the package 124 may be use to clean the inner thigh of the patient. Finally, the labeling 128 may state that the fifth wipe is used to clean a portion of the catheter 114. It is noted that the labeling 128 may instruct the user to perform the post-insertion patient care protocol in a different order, modify certain acts, and/or omit or add certain acts. For example, the labeling 128 may instruct the user to first clean a portion of the catheter 114 before cleaning the genitalia of the patient and/or clean the male shaft instead of the periphery about the male genitalia.

As previously discussed, the package 124 may include the token 126. The token 126 may be removed from the package 124 and attached to one of the indicator sites 122 (e.g., compliance indicator sites). Referring to FIG. 1B, the indicator element 104 is considered to be in an active state after the token 126 is removed from the package 124 and attached to an indicator site 122. For example, the indicator element 104 verifies that the post-insertion patient care protocol has been performed at least three times during a two day period. However, the indicator element 104 may also illustrate that the indicator element 104 does not verify that at least one post-insertion patient care protocol was performed.

Figure 1D:
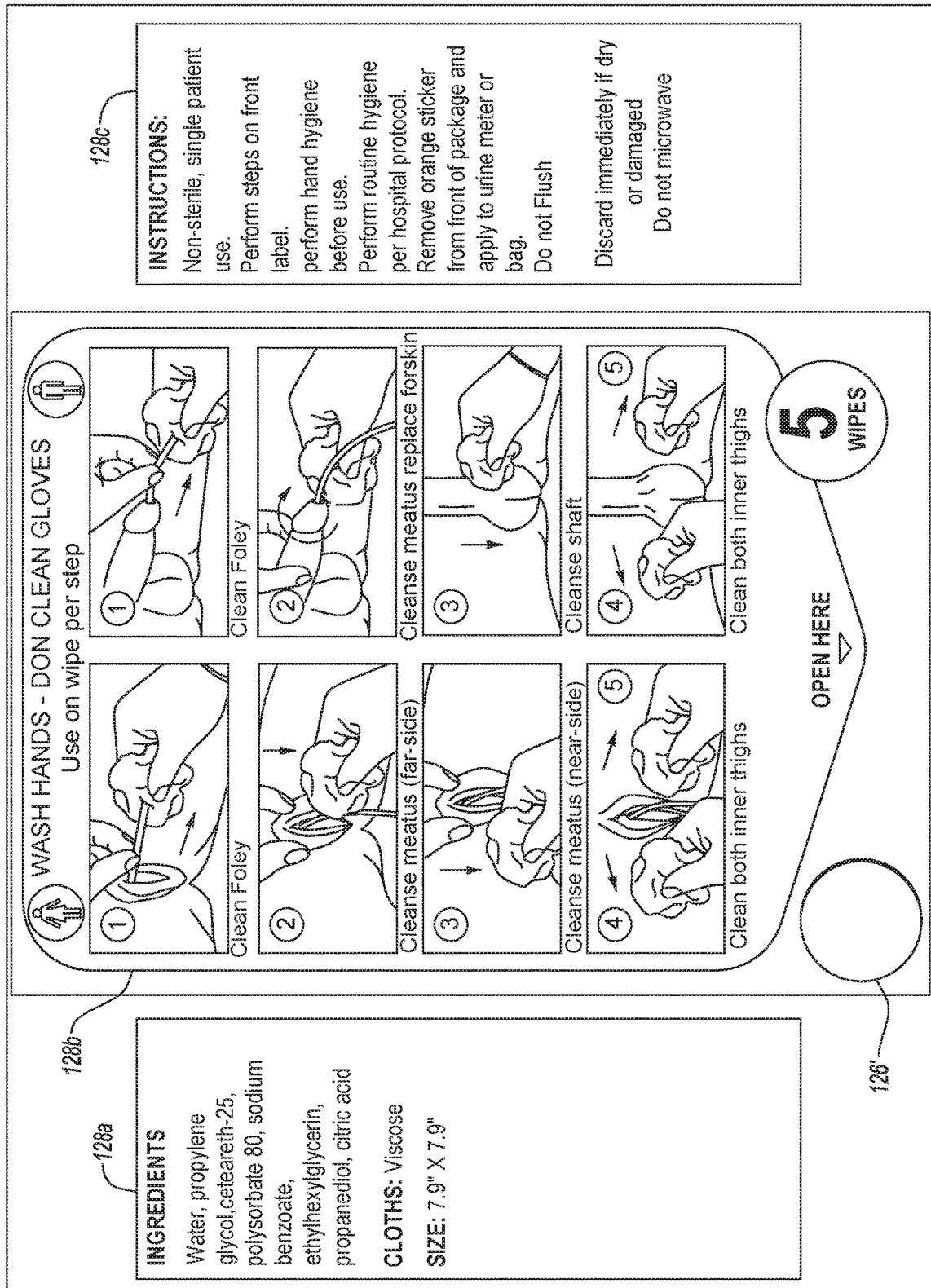
FIG. 1D is a top plan view of a package that may form a portion of the drainage bag system shown in FIG. 1A, according to an embodiment.

FIG. 1D is a top plan view of a package 124' that may form a portion of the drainage bag system 100, according to an embodiment. Except as otherwise described herein, the package 124' shown in FIG. 1D and its respective elements and components may be similar to or the same as the package 124 (FIG. 1C) and its respective elements and components. Additionally, the package 124' illustrated in FIG. 1D may be used with or used instead of the package 124 illustrated in FIG. 1C in any of the drainage bag systems disclosed herein.

The package 124' may include a plurality of distinct labelings thereon that facilitate performance and standardization of the post-insertion patient care protocol. In the illustrated embodiment, the plurality of distinct labelings may include a first labeling 128*a*, a second labeling 128*b*, and a third labeling 128*c*. The first labeling 128*a* may include general information related to the package 124', such as ingredients present in the package 124'. The second labeling 128*b* may state how the wipes present in the package 124' are to be used. For example, the second labeling 128*b* may state that the first wipe present in the package 124' may be used to clean a portion of the drainage bag system 100 (e.g., the catheter 114 shown in FIG. 1A), the second wipe present in the package 124' may be used to clean a meatus of a male patient or a far-side of a meatus of a female patient, the third wipe present in the package 124' may be used to clean a shaft of the male patient or a near-side of the meatus of the female patient, and the fourth and fifth wipes present in the package 124' may be used to clean both inner thigh regions of the patient. The second labeling 128*b* may include pictures (e.g., photographs, drawings, schematics, etc.) and/or words to convey how the wipes present in the package 124' are to be used. The third label 128*c* may state how the package 124' (e.g., not just the wipes present in the package 124') is to be used. For example, the third label 128*c* may state that the package 124' may be configured for single patient use, that the wipes present in the package 124' are to be used according to the second labeling 128*b*, that proper hand hygiene is to be performed before using the package 124', that hospital protocols are to be followed, a token 126' present on and/or in the package 124' is to be placed onto an indicator element, that the wipes present in the package 124' are not to be flushed down a toilet, etc.

In an embodiment, one or more of the first labeling 128*a*, the second labeling 128*b*, or the third labeling 128*b* may be used on the package 124 shown in FIG. 1C instead of the labeling 128. In an embodiment, one or more of the first labeling 128*a*, the second labeling 128*b*, or the third labeling 128*b* may be omitted from the package 124'. In an embodiment, the package 124' may include one or more additional labelings thereon. In an embodiment, all of the labels are placed on the same surface of the package 124'. In an embodiment, at least one of the labels are placed on a different surface of the package 124'. For example, at least one of the labels is placed on a front surface of the package 124' and at least one of the labels is placed on a back surface of the package 124'.

Figure 2:
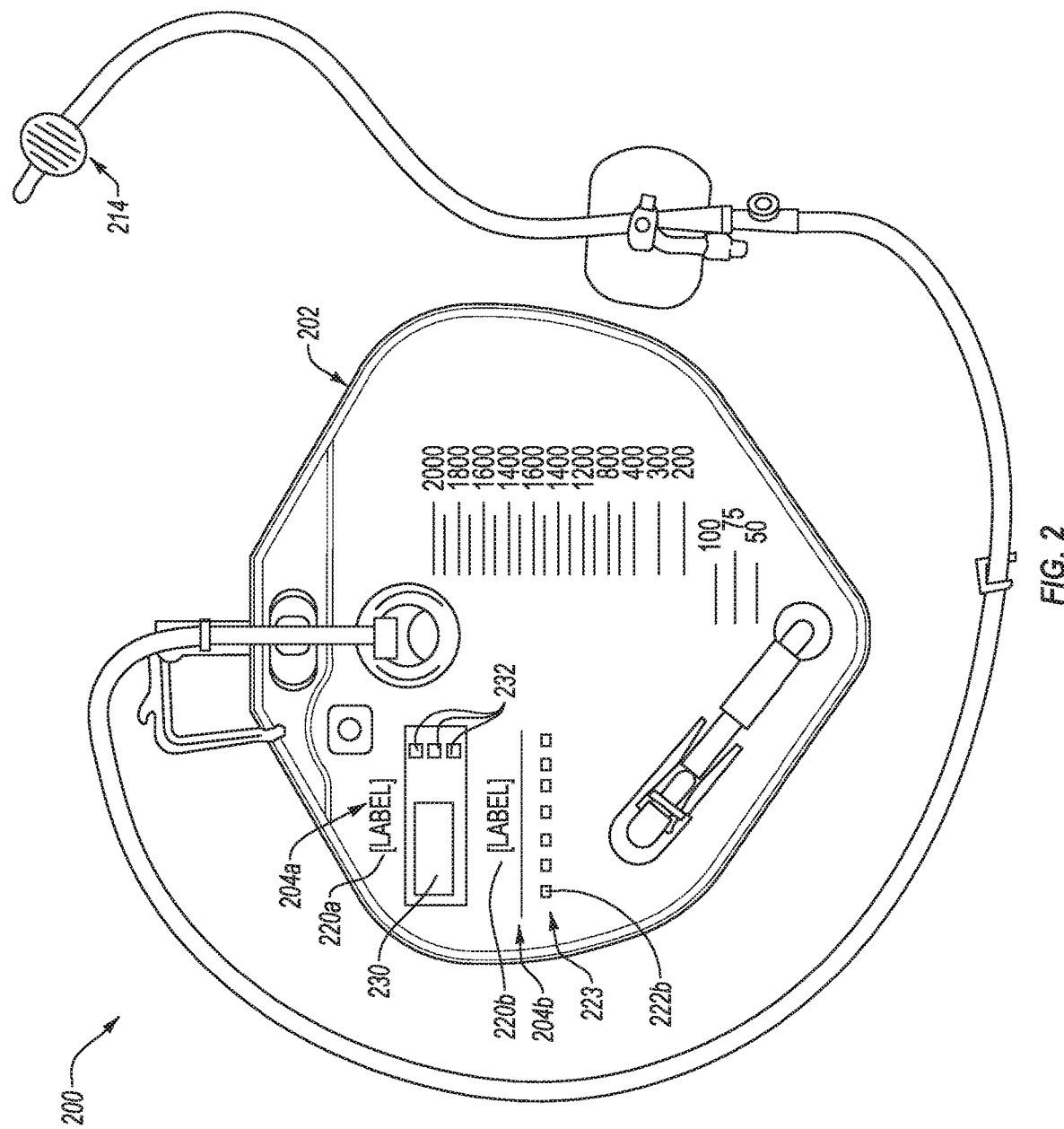
FIG. 2 is a top plan view of a drainage bag system that includes a drainage bag with a plurality of indicator elements, according to an embodiment.

FIG. 2 is a top plan view of a drainage bag system 200 that includes a drainage bag 202 with a plurality of indicator elements (e.g., two indicator elements), according to an embodiment. The drainage bag 202 may be similar to the drainage bag 102 shown in FIG. 1A. For example, the drainage bag 202 may be in fluid communication with a catheter 214. As mentioned above, the drainage bag 202 may include any suitable number of indicator elements. In the illustrated embodiment, the drainage bag 202 includes a first indicator element 204*a* and second indicator element 204*b*. However, the drainage bag 202 may include more or fewer than two indicator elements.

The first indicator element 204*a* may include a first type identifier 220*a* that may be marked by a user in any manner described above. In the illustrated embodiment, the first indicator element 204*a* also includes a display 230 (e.g., digital display) that provides or displays information to the user. The first indicator element 204*a* may also include one or more inputs 232 that may allow the user to interact with the first indicator element 204*a*. The inputs 232 may also allow the user to input any number and/or type of suitable information into the first indicator element 204*a*. For example, the inputs 232 may be used to input the insertion date of the catheter or other general information related to the drainage bag system 200 and/or patient care. As such, the display 230 may be a type identifier and, in some embodiments, the first type identifier 220*a* may be omitted. In another embodiment, the inputs 232 may be used to verify compliance with the one or more patient care protocols. As such, the display 230 may be an indicator site, such as a compliance indicator site. In particular, the display 230 may be inactive (e.g., the display 230 is blank (e.g., a blank location) and does not display information indicating (e.g., verifying) compliance with patient care protocols) and may be activated using the inputs 232. In some embodiments, the display 230 may be both a type identifier and an indicator site (e.g., compliance indicator site). In some embodiments, the first indicator element 204*a* may also include the display 230 and one or more indicator sites similar to any of the indicator sites disclosed herein.

In some embodiments, the first indicator element 204*a* may include a timer which may use the display 230 to show a time passed from an event and/or time left to an event. The event may include any act that is related to the drainage bag system 200. For example, the event may include the insertion of the catheter 114, the performance of one or more patient care protocols (e.g., the post-insertion patient care protocol), etc. In some embodiments, the user may use the one or more inputs 232 to indicate when an event occurred. For example, the user may use the one or more inputs 232 to enter a time, reset the timer, start the time, stop or pause the timer, etc. The first type identifier 220*a* may indicate the event that the display 230 is counting from and/or towards. In an embodiment, the digital display 230 may include memory that stores one or more instructions thereon and a processor that executes the one or more instructions stored on the memory. The user may input instructions into the digital display 230 using the inputs 232. The instructions may include when an event is to occur, what event occurred, or combinations thereof.

It should be appreciated that the timer may include any suitable timer, which may vary from one embodiment to the next. In some embodiments, the timer may be an electronic timer, which may be autonomously powered (e.g., may include one or more batteries or similar power supply sources) or may be connected to an external power supply (e.g., electrical outlet). Additionally or alternatively, the timer may include a mechanical mechanism that may be operated to change the time/date displayed to a user (e.g., wound to operate the display 230). Furthermore, in some embodiments, the timer may be controlled or operated by a chemical reaction (e.g., a chemical reaction may progressively cause or result in a change in color along a time and/or date scale, thereby indicating time elapsed after initiation of such reaction, which may be caused by user input).

In some embodiments, the first indicator element 204*a* may be removable and/or replaceable. For example, a user may remove the first indicator element 204*a* from the drainage bag 202 when replacing the drainage bag 202 and may place the first indicator element 204*a* on a new drainage bag. Alternatively or additionally, the user may attach the first indicator element 204*a* to any suitable location near the drainage bag 202. Moreover, any of the indicator elements described herein may be removable and/or replaceable.

In some embodiments, the first indicator element 204a may be configured to be tamper resistant and/or minimize falsification. For example, the first indicator element 204a may require a code before a user may input any information into the first indicator element 204a. In an embodiment, the code may be located inside a package. Alternatively, the code may be unique to the user thereby identifying the user.

The second indicator element 204b may include a second type identifier 220b that may receive input from a user in any manner described above. In the embodiment, the second indicator element 204b may also include a list or checklist 223. The list or checklist 223 may be at least partially formed from one or more second indicator sites 222b that may be substantially similar to any of the indicator sites disclosed herein. For example, the second indicator sites 222b may each initially include a blank or unfiled location configured to be marked by the user in any manner described therein. The list or checklist 223 may include second indicator sites 222b that do not correspond to a certain time or date. For example, the list or checklist 223 may be used when the one or more patient care protocols do not need to be performed at a certain time or date, when the second indicator sites 222b are configured to receive input that is configured to convey a time or date (e.g., each token corresponds to a date), when at least some of the second indicator sites 222b verify compliance with different patient care protocols (e.g., compliance indicator sites), etc.

While the first indicator element 204a and the second indicator element 204b are illustrated as including the display 230 and the list or checklist 223, respectively; it is understood that the first indicator element 204a and/or the second indicator element 204b may include any indicator element disclosed herein. For example, the first indicator element 204a and the second indicator element 204b may be substantially the same. Additionally, the drainage bag system 200 may further include more than two indicator elements. Moreover, as described above, one, some, or all of the indicator elements 204a, 204b may be tamper resistant.

As discussed above, the drainage bag system 200 may include an indicator element (e.g., the first indicator element 204a and/or the second indicator element 204b) thereon configured to verify compliance with one or more patient care protocols. For example, the indicator element may be configured to be marked using a writing utensil and/or a token that is associated with a package (e.g., the package 124, 124' shown in FIGS. 1C-1D). In some embodiments, the package may facilitate performance of one or more patient care protocols pre-insertion and/or post-insertion of a catheter. For example, a package that facilitates performance of one or more patient care protocols pre-insertion includes a kit, such as a Foley catheterization kit. In some embodiments, the writing utensil and/or token may be located in the kit.

Figure 3:
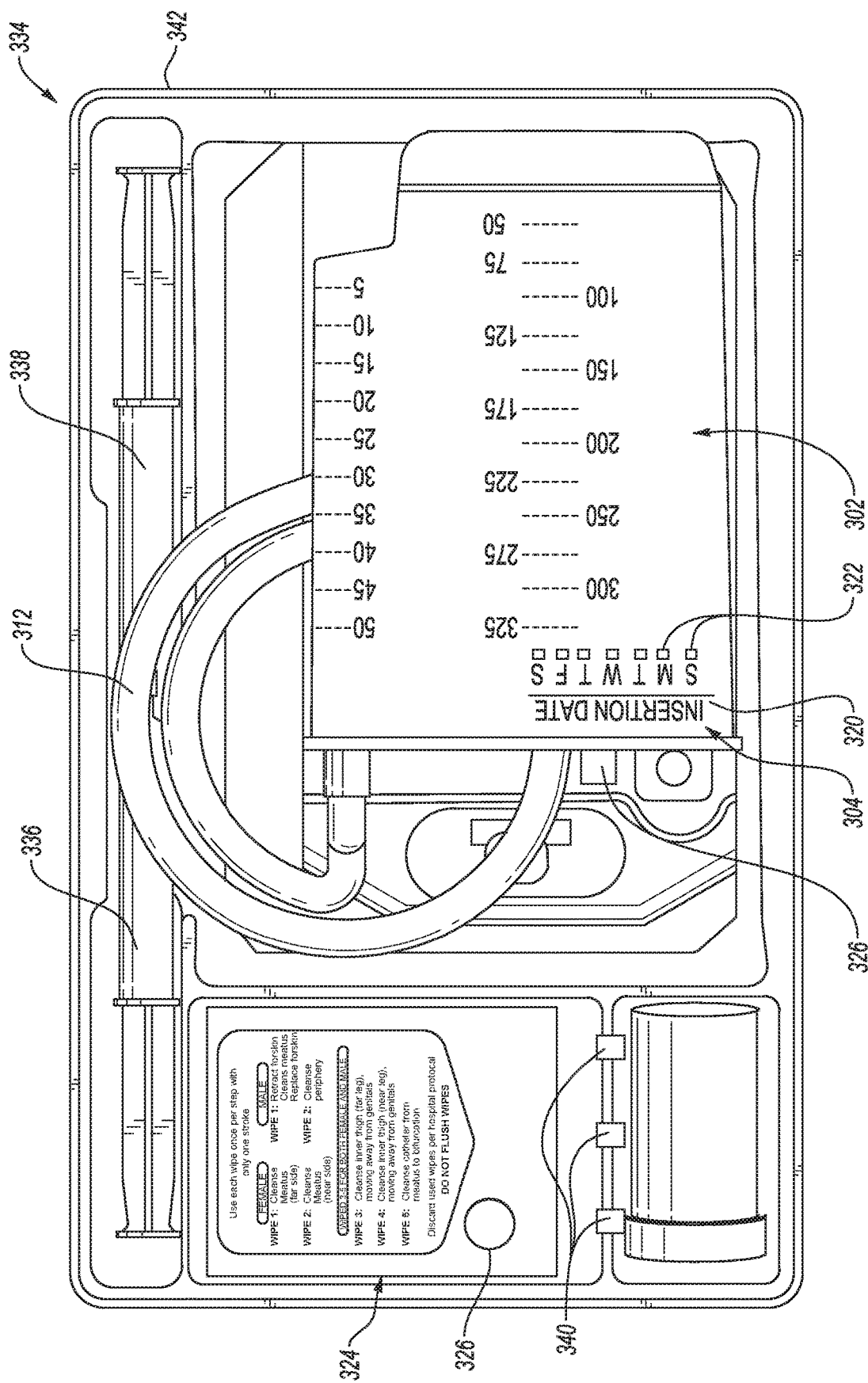
FIG. 3 is a top plan view of a kit that includes a drainage bag and at least one token, according to an embodiment.

For example, FIG. 3 is a top plan view of a kit 334 that includes a drainage bag 302 and one or more tokens 326, according to an embodiment. For example, the drainage bag 302 may include an indicator element 304 thereon that includes a type identifier 320 and/or one or more indicator sites 322. As described above, the one or more indicator sites 322 may be configured to have one or more tokens (e.g., token 326 and/or 326') attached thereto, thereby indicating compliance with one or more patient care protocols (e.g., compliance indicator sites). The kit 334 may include a catheter (not shown, obscured under drainage bag 302) and a drainage tube 312 connected or connectable to the drainage bag 302. In some embodiments, the kit 334 may be a Foley catheterization kit that may include sterile water 336 to inflate a balloon of the catheter, lubrication gel 338, one or more swabs 340, an antiseptic, at least one other suitable apparatus or device, or combinations of the foregoing. In some embodiments, the kit 334 may include a package 324 therein that that is used to perform one or more patient care protocols pre-insertion or post-insertions (e.g., the package 124, 124' shown in FIGS. 1C-1D). The package 324 may include at least one token 326 associated therewith or the token 326 associated with the package 324 may be omitted.

In an embodiment, the kit 334 may include a token 326 located in a tray 342 of the kit 334. For example, the token 326 may be accessed after the completion of one or more tasks related to the patient care and/or compliance with one or more patient care protocols displayed on the indicator element 304. The token 326 (e.g., the token located on the package 324 and/or the token located in the tray 342) may verify performance and/or compliance of a pre-insertion patient care protocol. More particularly, for example, the pre-insertion patient care protocol may include one or more of cleaning the catheter, the meatus of the patient, or the inner thighs of the patient using wipes present in the package 324 prior to insertion of the catheter into the patient.

In an embodiment, the token 326 located in the tray 342 may be located under the drainage bag 302. As such, the token 326 may be accessed after the drainage bag 302 is removed from the kit 334. Alternatively, the token 326 may be located at a number of other suitable locations in or on the tray 342 of the kit 334 (e.g., under the sterile water 336) or positioned on one or more components contained within the kit 334 (e.g., the sterile water 336, etc.). Additionally, marking the indicator element 304 using the token 326 within the kit 334 may indicate that the user marked the indicator element 304 at a time between opening and disposing the kit 334.

In some embodiments, the token 326 may be associated with a particular patient care protocol performed. For example, the kit 334 may include a plurality of tokens 326 therein that correspond to different patient care protocols. As such, the token 326 may include text, graphics, color, etc., which may associate the token 326 with the particular patient care protocol. Also, the token 326 may be located in any number of suitable kits or locations, which may be accessed during and/or after performing the particular patient care protocols.

In some embodiments, a separate pre-insertion patent care package may be included in the kit 334 and include its own corresponding one or more tokens to indicate performance and/or compliance of one or more pre-insertion patient care protocols including one or more of cleaning the catheter, the meatus of the patient, or the inner thighs of the patient using wipes present in the pre-insertion patent care package prior to insertion of the catheter into the patient. These separate one or more tokens from the pre-insertion patent care package may be applied to the indicator element 304 in a selected location to indicate performance and/or compliance of the one or more pre-insertion patient care protocols. As such, marking the indicator element 304 using the token may indicate that a specific task was completed (e.g., verifying that a pre-insertion and/or post-insertion patient care protocol was performed).

FIGS. 4A-4D are isometric views of indicator elements 404 that are distinct and separate from (e.g., not attached or otherwise incorporated into) a drainage bag 402, according to various embodiments. The indicator element 404 shown in FIGS. 4A-4D may be used in any of the embodiments disclosed herein.

The indicator elements 404 may be used in a drainage bag system 400 that is substantially similar to the drainage bag system 100 shown in FIG. 1A. For example, the drainage bag 402 may be configured to receive a fluid from a patient via a drainage tube 412. The drainage bag system 400 may also include at least one indicator element 404 that is configured to indicate that a task related to the drainage bag system 100 was performed. For example, the indicator element 404 may include a compliance indicator element configured to verify compliance with one or more patient care protocols that are associated with the drainage bag system 400. Each indicator element 404 may include a type identifier 420 and/or one or more indicator sites 422. Each indicator element 404 may include a paper, plastic, other medium, or combinations thereof that includes the type identifier 420 and/or the indicator sites 422 thereon (e.g., printed thereon).

Figure 4A:
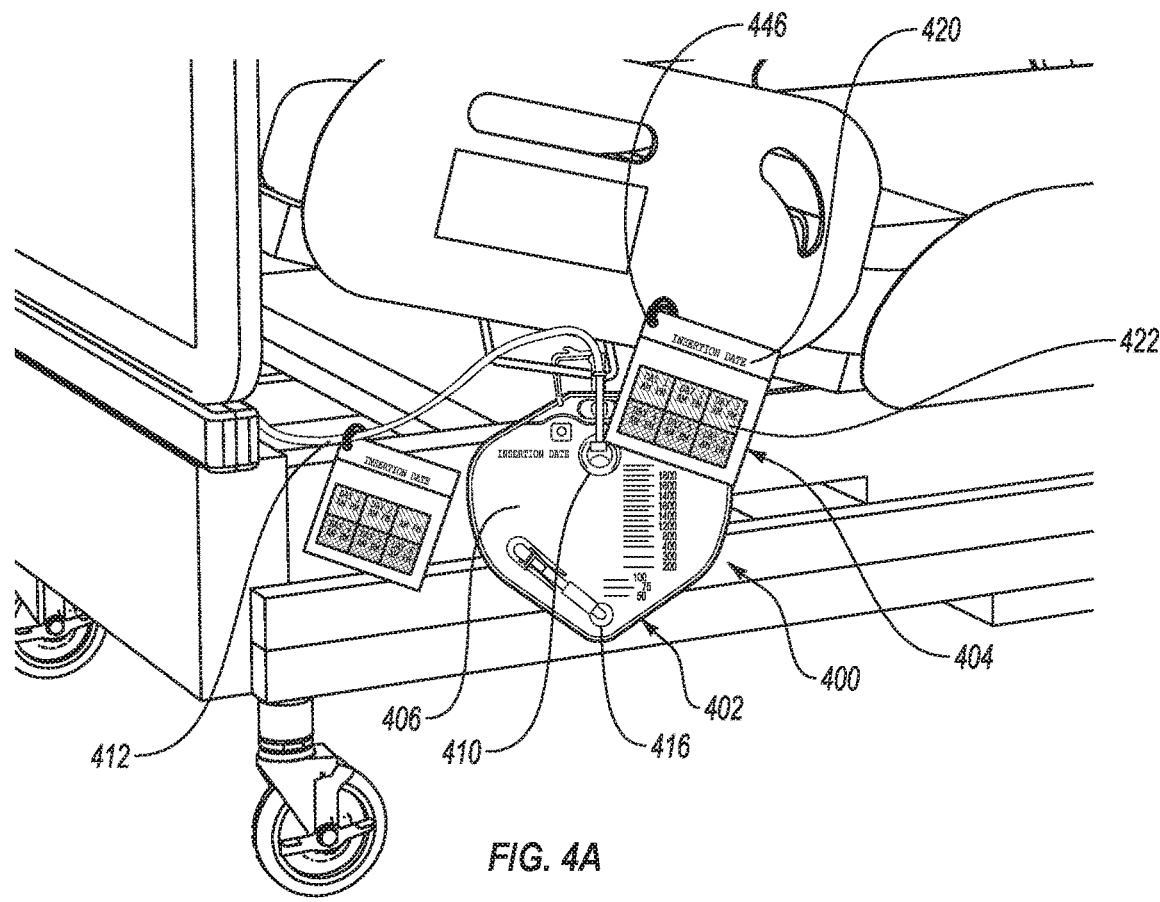
FIGS. 4A-4D are isometric views of indicator elements that are distinct and separate from a drainage bag, according to various embodiments.

Referring to FIG. 4A, the indicator element 404 may be configured to attach to one or more components of the drainage bag system 400. For example, the indicator element 404 is attached to one or more components of the drainage bag system 400 that are distinct and separate from the drainage bag 402, such as a drainage tube 412. Alternatively, the one or more components of the drainage bag system 400 may include a portion of the drainage bag 402 that is distinct and separate from the front panel 406, such as an inlet 410 of the drainage bag 402, an outlet 416 of the drainage bag 402, etc. The indicator element 404 may attach to the one or more components of the drainage bag system 400 using an adhesive, a string, an elastic band, a clamp, or another attachment method. For example, the indicator element 404 may include a hole 446 therein that receives the string, elastic band, or other attachment device. Alternatively, the hole 446 may receive the one or more components of the drainage bag system 400 (e.g., a portion of the drainage tube 412 may be positioned within the hole 446) or the hole 446 may be omitted. Similarly, the one or more components of the drainage bag system 400 may be configured to have the indicator element 404 attached thereto. For example, the one or more components of the drainage bag system 400 may comprises a stronger material or be thicker than similar portions of the drainage bag system 400.

Figure 4B:
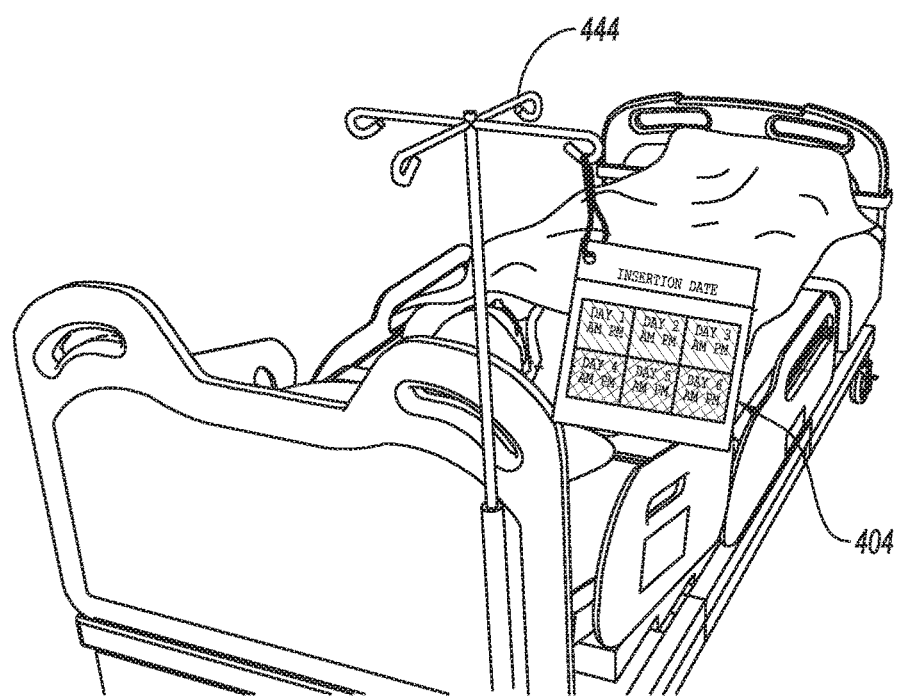

Referring to FIG. 4B, the indicator element 404 may be configured to be attach to one or more medical devices proximate to the drainage bag system 400. For example, the illustrated indicator element 404 is attached to an IV pole 444. The indicator element 404 may attach to the one or more medical devices using any of the attachment method disclosed herein.

Figure 4C:
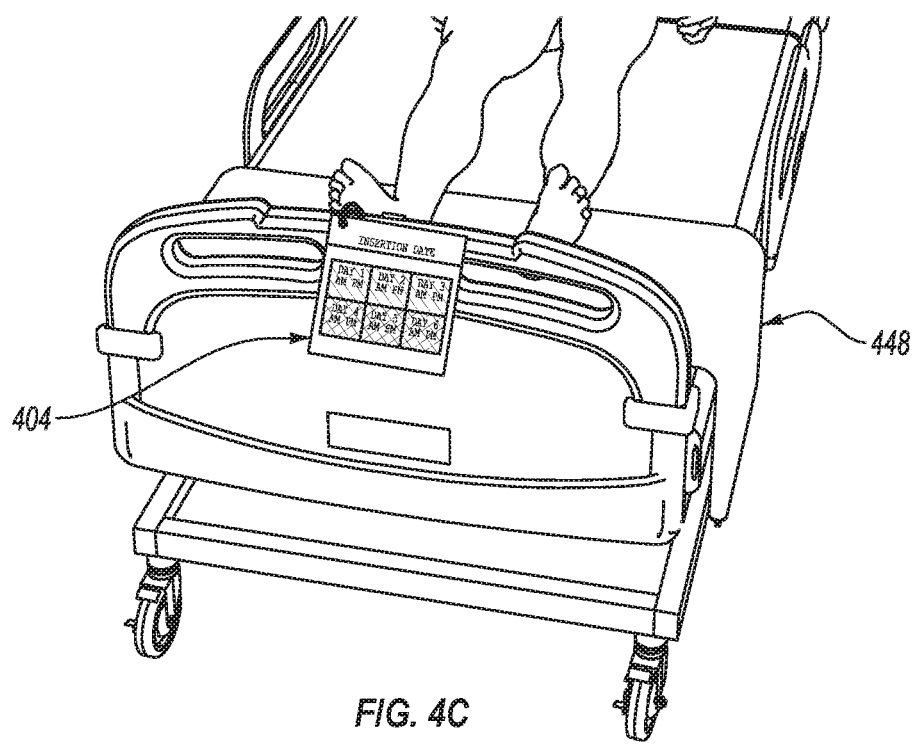

Referring to FIG. 4C, the indicator element 404 may be configured to be attached to a bed 448. For example, the indicator element 404 may be attached to the bed 448 on which a patient is positioned. The indicator element 404 may be attached to any portion of the bed 448, such as a base of the bed 448. The indicator element 404 may be attached to the bed 448 using any of the attachment methods disclosed herein.

Figure 4D:
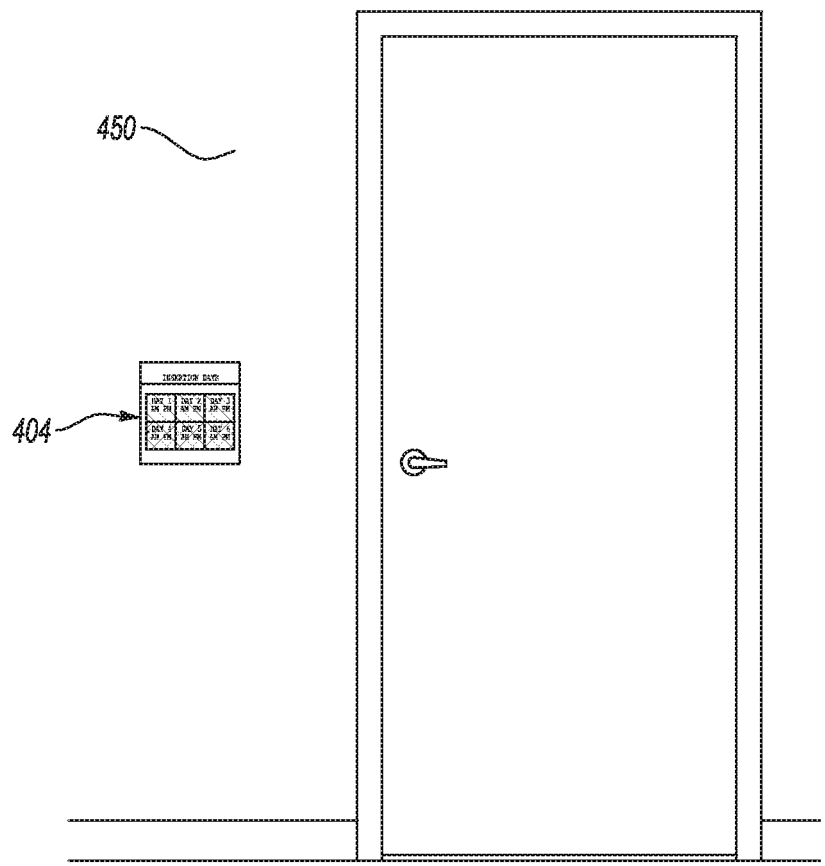

Referring to FIG. 4D, the indicator element 404 may be configured to be attached to a wall 450. For example, the indicator element 404 may be attached to one of the walls 450 that encloses a room in which the drainage bag system 400 is positioned. The indicator element 404 may be attached to the wall 450 using any of the attachment techniques and/or devices disclosed herein.

In an embodiment, the indicator element 404 may distinct and separate from the drainage bag 402 to improve the visibility of the indicator element 404 from one or more locations. For example, the drainage bag 402 may be at least partially obscured from one or more locations (e.g., the door to the patient's room, the base of the bed 448, etc.). As such, the indicator element 404 may be spaced from the drainage bag 402 and attached to a location that improves the visibility of the indicator element 404 from one or more locations, such as any of the locations disclosed herein or any other suitable location.

Figure 5:
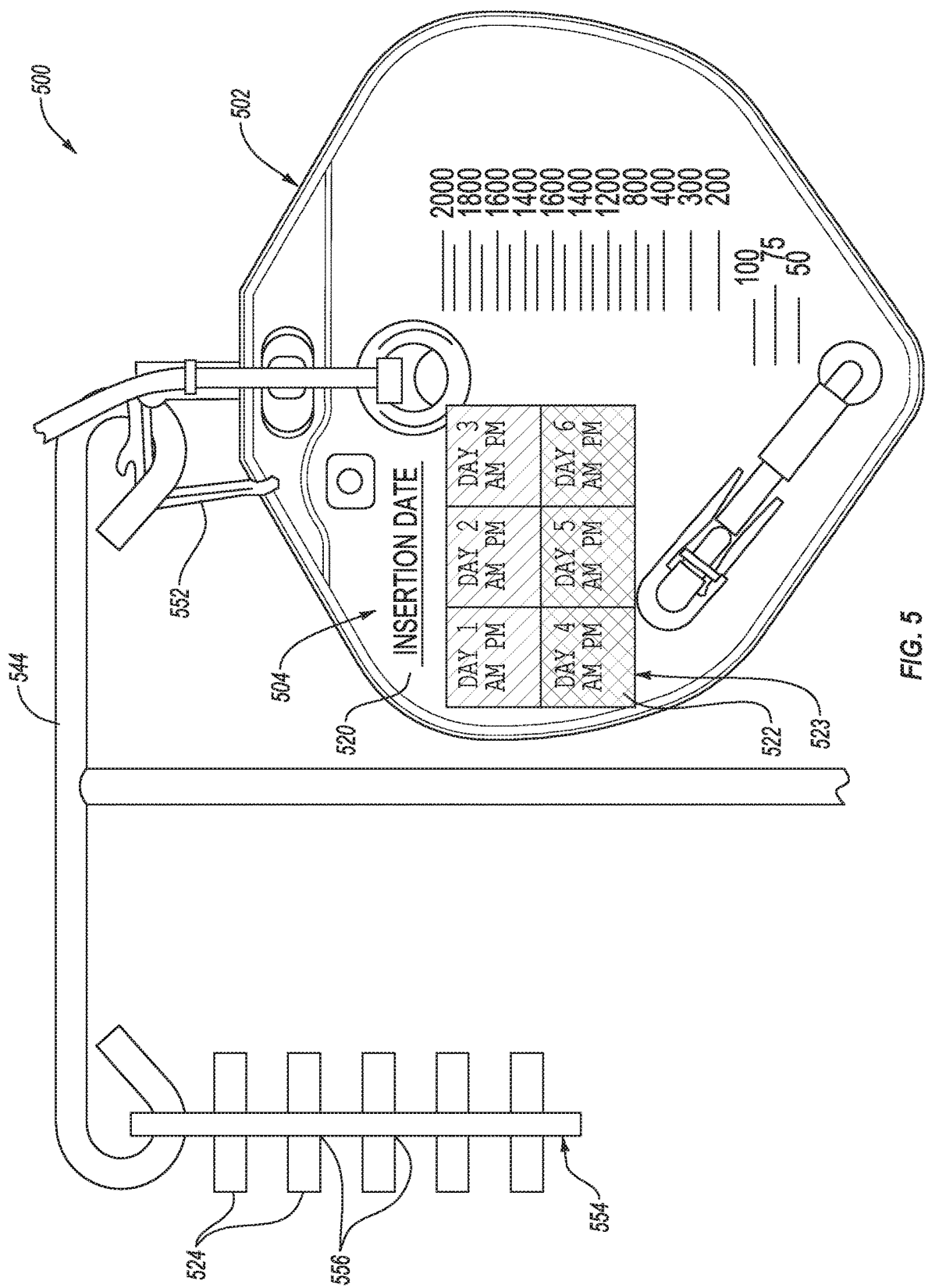
FIG. 5 is a side view of a drainage bag system including a drainage bag and a plurality of packages removably attached together, according to an embodiment.

FIG. 5 is a side view of a drainage bag system 500 including a drainage bag 502 and a plurality of packages 524 (e.g., the package 124, 124' shown in FIGS. 1C-1D) removably attached together, according to an embodiment. The plurality of packages 524 may be used with any of the embodiments disclosed herein.

The drainage bag 502 may be the same as or similar to the drainage bags 102, 202, 302, 402 shown in FIGS. 1A, 2-4A. For example, the drainage bag 502 may include at least one indicator element 504 configured to verify completion of a task related to the drainage bag system 500. In the illustrated embodiment, the indicator element 504 includes a type identifier 520 and one or more indicator sites 522. The indicator sites 522 may at least partially form a calendar 523. Each of the one or more indicator sites 522 may include a blank or unfilled location that is configured to be marked by a user. For example, the one or more indicator sites 522 may be marked by a user before, during, or after one or more patient care protocols have been performed. In the illustrated embodiment, the indicator element 504 may include a compliance indicator sites that may verify compliance with one or more patient care protocols that occur twice a day (e.g., every 12 hours).

In an embodiment, the drainage bag 502 may be configured to be attached to an IV pole 544. For example, the drainage bag 502 may include a hook 552 that attaches to the IV pole 544. Connecting the drainage bag 502 to the IV pole 544 or another similar device may increase the visibility of the indicator element 504. However, the drainage bag 502 may be attached to devices other than the IV pole 544 that are proximate the patient. For example, the drainage bag 502 may be attached to the patient, a bed, a wheelchair, a medical device, a wall, or any other suitable device.

The plurality of packages 524 may be removably attached together (e.g., directly or indirectly). In the illustrated embodiment, the plurality of packages 524 are indirectly attached together used a retention device 554. The retention device 554 may be attached to the IV pole 544 (e.g., include a hook, hole, etc.). The retention device 554 may include any device that is configured to carry the plurality of packages 524 and permit the packages 524 to be removed therefrom. For example, the retention device 554 may include a rigid, semi-rigid, or flexible material. Each of the plurality of packages 524 may be attached to the retention device 554 using adhesives (e.g., both weak and strong adhesives), clamps, or any other attachment technique. In an embodiment, each of the plurality of packages 524 may be removably attached to the retention device 554, thereby allowing each of the plurality of packages 524 to be selectively detached from the retention device 554 and from each other. For example, in the illustrated embodiment, the retention device 554 may define a plurality of holes 556 that can receive the plurality of packages 524. In another embodiment, the plurality of packages 524 may be attached to the retention device 554 using a weak adhesive or other reversible attachment technique. In another embodiment, each of the plurality of packages 524 may more strongly attached (e.g., using a strong adhesive, a staple, etc.) to the retention device 554. For example, in such an embodiment, detaching one of the plurality of packages 524 from the rest of the packages 524 also requires separating some of the retention device 554 from the rest of the retention device 554. As such, the retention device 554 may include a plurality of perforations or other mechanism that permits a portion of the retention device 554 to be separated from the rest of the retention device 554.

In an embodiment, the plurality of packages 524 may be directly removably attached together. For example, the plurality of packages 524 are removably attached together using an adhesive that is strong enough to hold the plurality of packages 524 together, but weak enough to allow each of the plurality of packages 524 to be detached without damaging the any of the plurality of packages 524. In another embodiment, each of the plurality of packages 524 may be bonded together. In such an example, the boundary between each of the plurality of packages 524 may include a plurality of perforations that allow a user to easily separate one package 524 from an immediately adjacent package 524. In an embodiment, the plurality of packages 524 may be removably attached to each other and to the retention device 554.

The plurality of packages 524 may be configured to verify compliance with one or more patient care protocols. For example, detaching one of the plurality of packages 524 from the rest of the plurality of packages 524 may indicate that one or more patient care protocols associated with the packages 524 has been performed. A compliance officer (e.g., a supervisor, responsible physician, etc.) may view the plurality of packages 524 and see that at least one package 524 is missing, thereby indicating that the one or more patient care protocols associated with the package 524 were performed.

In an embodiment, the plurality of packages 524 may be used in conjunction with the indicator element 504 of the drainage bag 502. For example, each of the plurality of packages 524 may include at least one token associated therewith (e.g., attached thereto, incorporated therewith, or positioned therein). In some embodiments, the token may only be accessed after the package 524 is detached from the rest of the plurality of packages 524. As such, the plurality of packages 524 may form a second means of indicating compliance with the one or more patient care protocols.

While various aspects and embodiments have been disclosed herein, other aspects and embodiments are contemplated. The various aspects and embodiment disclosed herein are for purposes of illustration and are not intended to be limiting.

What is claimed:

1. A drainage bag system, comprising:
   a drainage bag including:
      an inlet configured to receive a fluid from a patient;
      one or more panels defining an interior space configured to hold the fluid therein; and
      at least one indicator element disposed on the one or more panels, the at least one indicator element including one or more indicator sites thereon, each of the one or more indicator sites including at least one of a blank or unfilled location corresponding to one or more catheter post-insertion patient care protocols; and
   one or more patient care protocol packages including at least one token associated therewith, the one or more indicator sites are configured to be marked with the at least one token;
   wherein the one or more catheter post-insertion patient care protocols include, while a catheter is positioned in the patient, washing at least one of a perineal region of the patient, a periurethral region of the patient, a genitalia of the patient, or one or more portions of the drainage bag system.

2. The drainage bag system of claim 1 wherein the at least one indicator element is attached to the drainage bag.

3. The drainage bag system of claim 1 wherein the at least one indicator element is distinct from the drainage bag.

4. The drainage bag system of claim 1 wherein the at least one indicator element is configured to be marked with a writing utensil.

5. The drainage bag system of claim 1 wherein the at least one indicator element is configured to be marked with at least one token.

6. The drainage bag system of claim 1 wherein the at least one indicator element includes a calendar, the calendar at least partially formed from the one or more indicator sites, one or more of the one or more indicator sites corresponding to at least one of a date, day, or time.

7. The drainage bag system of claim 1 wherein the at least one indicator element includes a list or a checklist, the list or the checklist at least partially formed from the one or more indicator sites.

8. The drainage bag system of claim 1 wherein the at least one indicator element includes a display.

9. The drainage bag system of claim 1 wherein the one or more patient care protocol packages include at least one of a container including wipes therein, a catheterization kit, a syringe configured to remove the fluid from the interior of the drainage bag, or a container including gloves therein.

10. The drainage bag system of claim 1 wherein the one or more patient care protocol packages include labeling printed thereon, the labeling detailing at least one of how the one or more catheter post-insertion patient care protocols are to be performed or how the package is to be used.

11. The drainage bag system of claim 1 wherein the at least one token is attached to an exterior surface of the one or more patient care protocol packages, the at least one token covering a portion of the one or more patient care protocol packages that is configured to grant access to an interior region of the one or more patient care protocol packages.

12. The drainage bag system of claim 1, further comprising a retention device including the one or more patient care protocol packages removably attached thereto.

13. The drainage bag system of claim 1 wherein the one or more indicator sites include one or more compliance indicator sites for indicating compliance with one or more catheter post-insertion patient protocols.

14. The drainage bag system of claim 1 wherein the at least one indicator element is attached to at least one of the one or more panels, a privacy barrier integrally formed with the drainage bag, or another component of the drainage bag system that is separate from the drainage bag.

15. A method of using a drainage bag, the method including:
   providing a drainage bag system to be operably connected to a patient, the drainage bag system including:
      the drainage bag including one or more panels defining an interior space configured to contain fluid; and
      at least one indicator element disposed on the one or more panels, the at least one indicator element including one or more indicator sites thereon, each of the one or more indicator sites including at least one of a blank or unfilled location;

performing one or more catheter post-insertion patient care protocols on the patient related to using the drainage bag with the patient with one or more patient care protocol packages;

wherein the one or more catheter post-insertion patient care protocols include, while a catheter is positioned in the patient, washing at least one of a perineum region of the patient, a periurethral region of the patient, a genitalia of the patient, or one or more portions of the drainage bag system;

removing at least one token from the one or more patient care protocol packages, the at least one token associated with the package; and marking the one or more indicator sites with the at least one token to show that the one or more catheter post-insertion patient care protocols were performed.

16. The method of claim 15 wherein marking the one or more indicator sites includes marking at least one of the one or more indicator sites with at least one of a writing utensil or at least one token.

17. The method of claim 15, further comprising:

performing one or more catheter pre-insertion patient care protocols on the patient related to using the drainage bag with the patient; and marking the one or more indicator sites to show that the one or more catheter pre-insertion patient care protocols were performed.

18. The method of claim 15 wherein the one or more indicator sites include one or more compliance indicator sites for verifying compliance with the one or more catheter post-insertion patient protocols, and wherein marking the one or more indicator sites to show that the one or more catheter post-insertion patient care protocols were performed includes marking the one or more compliance indicator sites to show compliance with the one or more catheter post-insertion patient protocols.

19. The method of claim 15 wherein providing a drainage bag system to be operably connected to a patient includes operably connecting the drainage bag system to the patient.

20. The method of claim 15 wherein the at least one indicator element is positioned on the drainage bag.

21. The method of claim 15 wherein the at least one indicator element is separate from the drainage bag.

22. A drainage bag system, comprising:

a drainage bag including:
an inlet configured to receive a fluid from a patient; and
one or more panels defining an interior space configured to hold the fluid therein;
at least one indicator element disposed on the one or more panels, the at least one indicator element including one or more indicator sites thereon, each of the one or more indicator sites including at least one of a blank or unfilled location corresponding to one or more catheter post-insertion patient care; and one or more patient care protocol packages including at least one token associated therewith;

wherein the one or more indicator sites are configured to be marked with the at least one token.

* * * * *